(12) United States Patent
Combette et al.

(10) Patent No.: US 7,214,478 B2
(45) Date of Patent: *May 8, 2007

(54) COMPOSITE MATERIAL FOR BIOLOGICAL OR BIOCHEMICAL ANALYSIS MICROFLUIDIC SYSTEM

(75) Inventors: Philippe Combette, Montpellier (FR); Frédéric Revol-Cavalier, Seyssins (FR); Frédérique Mittler, St Egreve (FR); Bernard Beneyton, Le Fontainil Cornillon (FR)

(73) Assignee: Commissariat a l'Energie Atomique, Paris (FR)

( * ) Notice: Subject to any disclaimer, the term of this patent is extended or adjusted under 35 U.S.C. 154(b) by 92 days.

This patent is subject to a terminal disclaimer.

(21) Appl. No.: 10/475,634

(22) PCT Filed: Feb. 20, 2003

(86) PCT No.: PCT/FR03/00567

§ 371 (c)(1),
(2), (4) Date: Oct. 20, 2003

(87) PCT Pub. No.: WO03/071277

PCT Pub. Date: Aug. 28, 2003

(65) Prior Publication Data

US 2004/0126779 A1 Jul. 1, 2004

(30) Foreign Application Priority Data

Feb. 21, 2002 (FR) .................... 02 02206

(51) Int. Cl.
*C12Q 1/68* (2006.01)
(52) U.S. Cl. .............................. 435/4; 435/6
(58) Field of Classification Search ............... None
See application file for complete search history.

(56) References Cited

U.S. PATENT DOCUMENTS 5,124,128 A 6/1992 Hildenbrand et al.

OTHER PUBLICATIONS

Duffy, D. C., et al., "Rapid Prototyping of Microfluidic Systems in Poly(dimethylsiloxane)", *Analytical Chemistry, Amer. Chem, Soc.*, XP-002149044, 70: 4974-4984, 1998.

*Primary Examiner*—James Ketter
(74) *Attorney, Agent, or Firm*—Hutchison Law Group PLLC

(57) ABSTRACT

The invention concerns a component for biological or biochemical analysis microsystems formed from a support and having at least one chemically functionalised surface zone, in order to allow in said zone the formation of a chemistry for anchoring biological or biochemical elements, and/or electrically, in order to allow in said zone the formation of electrical charges. The support comprises at least one part (21) formed of a composite material, said composite material being a mixture of at least one inert material and at least one chemically and/or electrically functionalisable material to provide said functionalised surface zone.

7 Claims, 3 Drawing Sheets

COMPOSITE MATERIAL FOR BIOLOGICAL OR BIOCHEMICAL ANALYSIS MICROFLUIDIC SYSTEM

DESCRIPTION

1. Technical Field

The present invention concerns a component for biological or biochemical analysis microsystems, said component using a composite material. It further concerns a method for producing said component.

2. State of the Prior Art

A microsystem for biological or biochemical analysis is produced from a support or substrate chosen so that a surface (which may comprise several zones) of said support or substrate provides one or several functions. Said function(s) may be a chemical functionally or an electrical functionality.

Chemical functionality is involved when biological or biochemical elements have to be anchored to the support. Generally, the supports are in glass or silica, which allows the anchoring of biological or biochemical elements by a well controlled coupling chemistry, for example by silanisation.

Electrical functionality is involved for the circulation of fluids in micro-channels or micro-reservoirs. Fluid circulation microsystems generally use electrokinetic pumping, such as electro-osmosis, to make fluids circulate in the micro-channels and micro-reservoirs formed in the supports. Said pumping means require the existence of electrically active surfaces. It is the use of high electrical fields, combined with the presence of electrically active surfaces, that makes fluid flow possible. Known supports, in glass or silica, are well suited to said pumping means.

Glass or silicon supports are therefore well suited to obtaining chemical and electrical functionalities.

Reference is increasingly made to the use of inert materials such as polymers, plastics, and adhesives in producing said microsystems. However, the chemistry for anchoring biological or biochemical elements on said inert materials depends on their chemical formulation and remains awkward to implement. Materials such as moulded plastics for forming micro-channels and photosensitive polymers or resins for forming microstructures would be very widely used if it were possible to easily anchor biological or biochemical elements to them. Indeed, said materials are cheap and are used in large production series.

Furthermore, electrokinetic flow is problematic in materials such as conventional polymers and requires the use of costly techniques such as plasma activation in order to generate electrically charged surfaces. However, it has been shown that this does not allow the treated surface to be activated definitively. Consequently, the system evolves over time.

DESCRIPTION OF THE INVENTION

The present invention provides a solution to the problems described above. It allows the use of chemically inert materials (polymers, resins, plastics, adhesives, etc.) to form component supports for biological or biochemical analysis microsystems, said inert materials being used in combination with a functionalisable material in order to allow the anchoring of biological or biochemical elements. Said biological or biochemical elements may then be grafted by conventional techniques, for example by a silanisation technique.

The biologically or biochemically functionalisable material is incorporated directly into the inert material (plastic, adhesive) to obtain a composite material. Several solutions may be envisaged to obtain said composite material.

One solution consists in forming a mixture of two liquid phases which, after several technological steps, are congealed in the form of a composite material. One of the phases (for example, synthetic silica) makes it possible to assure the functionalisation by an anchoring chemistry in an identical manner to that formed on a glass substrate (for example, silanisation).

Another solution consists in mixing, either directly with a plastic comprising the inert material, or a photosensitive or non-photosensitive polymer, elements (preferably beads) in silica, in glass, in metal or in functionalisable polymer. Said beads assure the attachment of the biological or biochemical elements and have the further advantage of increasing the anchoring surface for the biological or biochemical elements.

If a photosensitive material is used as inert material, the composite material obtained thereof makes it possible to form structured components by the methods used in microtechnology. The functionalisation again takes place either on the dispersed phase in the photosensitive material, or on the elements included in said material.

The deposited material may also be a material providing an electrical functionality to the component, which allows the circulation of fluids by electrokinetic pumping.

Consequently, the aim of the invention is a component for biological or biochemical analysis microsystems formed from a support and having at least one chemically functionalised surface zone, in order to allow in said zone the formation of a chemistry for anchoring biological or biochemical elements, and/or electrically, in order to allow in said zone the formation of electrical charges, characterised in that said support comprises at least one part formed of a composite material, said composite material being a mixture of at least one inert material and at least one chemically and/or electrically functionalisable material to provide said functionalised surface zone.

Preferably, the inert material of the composite material is a material chosen from among a polymer, a plastic, a resin and an adhesive. The polymer may be a polyimide, a poly (dimethylsiloxane) or an epoxy type photosensitive resin.

Said part may form the support in its entirety.

The support may comprise a substrate supporting said part. The substrate may be in a material chosen from among glass, silica, silicon, a polymer and a metal.

Said part may be structured.

Advantageously, the functionalisable material is chosen from among silica, synthesised silica, silicon nitride, a metal and a functionalisable polymer.

The composite material may be a mixture comprising a phase of inert material and a phase of functionalisable material.

It may also be formed of elements of a functionalisable material dispersed in the inert material. The functionalisable material may be in the form of beads.

Said surface zone may support chemical functions suited to assuring the attachment of biological elements or other chemical functions on said surface zone.

Said surface zone may support chemical functions suited to assuring the presence of electrical charges on said surface zone.

A further aim of the invention is a method for producing a component for biological or biochemical analysis microsystems from a support, said support needing to have at least one chemically functionalised surface zone to allow in said zone the formation of a chemistry for anchoring biological or biochemical elements, and/or electrically, to allow in said zone the formation of electrical charges, characterised in that it comprises forming a support comprising at least one part in composite material, said composite material being a mixture of at least one inert material and at least one chemically and/or electrically functionalisable material in order to provide said functionalised surface zone.

According to a first embodiment, the composite material may be obtained by mixing in liquid phases the inert material and the functionalisable material, the mixture then being solidified in order to provide said part in composite material.

According to a second embodiment, the composite material may be obtained by dispersion of elements in functionalisable material in the inert material in liquid phase, the mixture then being solidified in order to provide said part in composite material. Preferably, said elements in functionalisable material are in the form of beads.

The inert material in liquid phase in which are dispersed said elements may be poured onto a support with impression(s) before being solidified.

The support with impression(s) may be removed after solidification of the mixture.

The inert material in liquid phase in which are dispersed said elements may be deposited on a support before being solidified. If the inert material is a photosensitive material, said part in composite material may be, after solidification, structured by photo-lithography. If the deposition is made on one surface of the support having at least one impression, the composite material may be, after solidification, eliminated outside of the impression. If the inert material is a photosensitive material, the elimination of the composite material outside of the impression may be achieved by photo-lithography.

According to a third embodiment, the support having one face with at least one impression, the elements in functionalisable material are deposited at the base of the impression, then the inert material in liquid phase is poured onto said face of the support, then the inert material is solidified to provide the composite material at the base of the impression, the support being finally removed. Advantageously, said elements in functionalisable material are in the form of beads.

Whatever the embodiment, the solidification may be obtained by a thermal treatment.

BRIEF DESCRIPTION OF THE DRAWINGS

The invention will be more fully understood and other advantages and specific features will become clearer on reading the description given hereafter, given by way of indication and in nowise limitative, and by referring to the appended drawings among which.

DETAILED DESCRIPTION OF EMBODIMENTS OF THE INVENTION

Figure 1A:
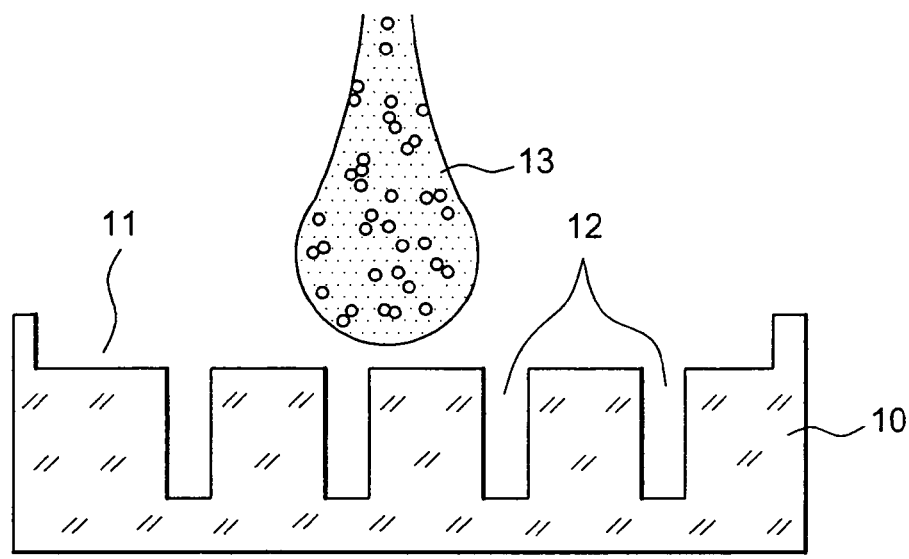
FIGS. 1A and 1B are cross-sectional views illustrating the formation of a first component for biological or biochemical analysis microsystems according to the invention.
Figure 1B:
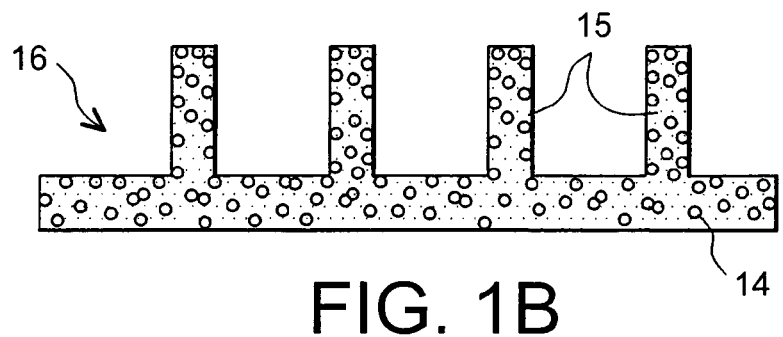

FIGS. 1A and 1B illustrate the formation of a component for biological or biochemical analysis microsystems according to the invention using a support with impression(s).

FIG. 1A shows a support 10, for example in silicon, in which the upper face has been machined or etched to form an impression consisting in a depression 11 prolonged by trenches 12. One pours onto the impression a mixture of a liquid composite material 13 formed of a polymer (for example poly (dimethylsiloxane)) and microbeads (for example silica microbeads of 1 μm diameter). The quantity of liquid composite material is provided to entirely fill the impression.

The support and its contents are then placed in an oven maintained at 60° C. for 4 hours.

After evacuation of the solvents contained in the polymer, the composite material is unmolded from the support. The component 16 obtained thereof is represented in FIG. 1B. It comprises a base 14 that complements the depression 11 and walls 15 perpendicular to the base and that complements the trenches 12. Two consecutive walls define a channel. The resulting component is ready to undergo chemical and/or electrical protocols allowing it to be functionalised.

Figure 2A:
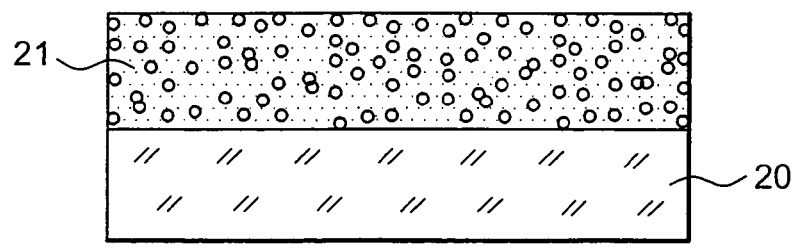
FIGS. 2A and 2B are cross-sectional views illustrating the formation of a second component for biological or biochemical analysis microsystems according to the invention.
Figure 2B:
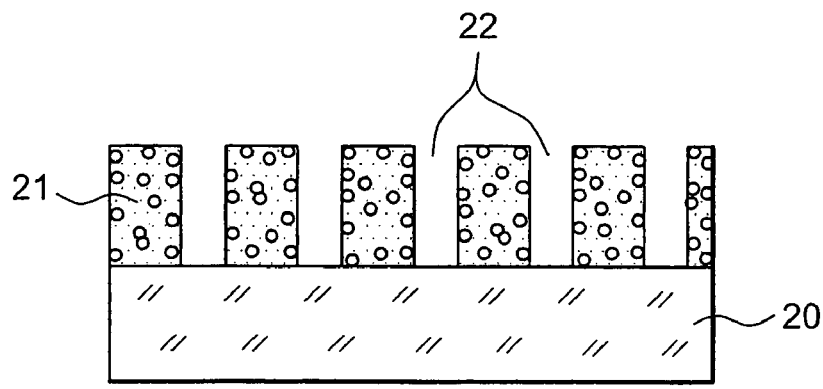

FIGS. 2A and 2B illustrate the formation of a component for biological or biochemical analysis microsystems from a photosensitive composite material.

Patterns in photosensitive polymer or resin may be formed on flat substrates, which avoids the use of complex etching machines. For example, the formation of blocks or channels in a glass or silicon sheet is replaced by a simple photo-lithography.

Deep etching of glass is awkward. It cannot be achieved by plasma due to the blocking of the etching by the ionic and metallic impurities contained within the glass. The glass is therefore etched by isotropic chemical means, which precludes the formation of fine patterns of small pitch. The invention makes it possible to form such structures using a photosensitive composite material.

FIG. 2A shows a 100 mm diameter support 20 in silicon in which the upper face is covered with a layer of composite material 21. Said composite material is formed of a commercially available photosensitive polyimide called "Probimide 7510" in which are dispersed microbeads, for example 1 μm diameter silica microbeads. The mixture is deposited with a spin coater on the support 20 at a speed of 3000 rpm then annealed at 110° C. on a heating plate.

The composite material is radiated by ultra violet rays through a mask then developed in order to obtain the desired component, for example that shown in FIG. 2B where trenches 22 can be seen in the composite material 21. Then, the composite material is annealed at 150° C. on a heating plate, then at 300° C. in a thermal treatment oven.

Figure 3A:
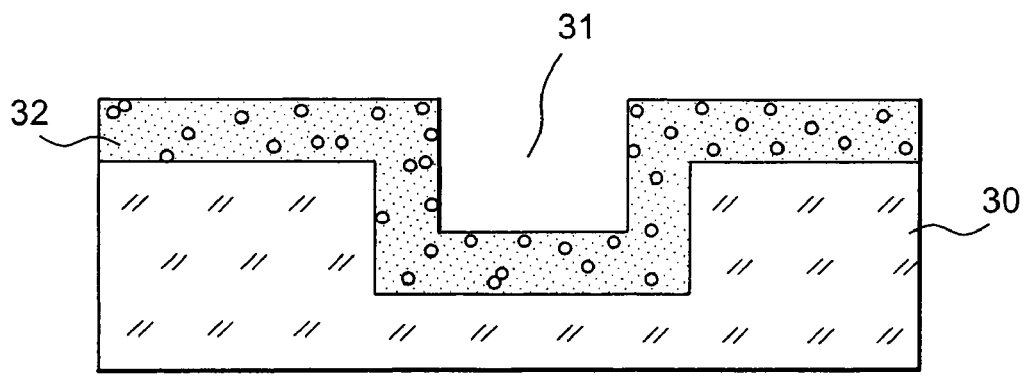
FIGS. 3A and 3B are cross-sectional views illustrating the formation of a third component for biological or biochemical analysis microsystems according to the invention.
Figure 3B:
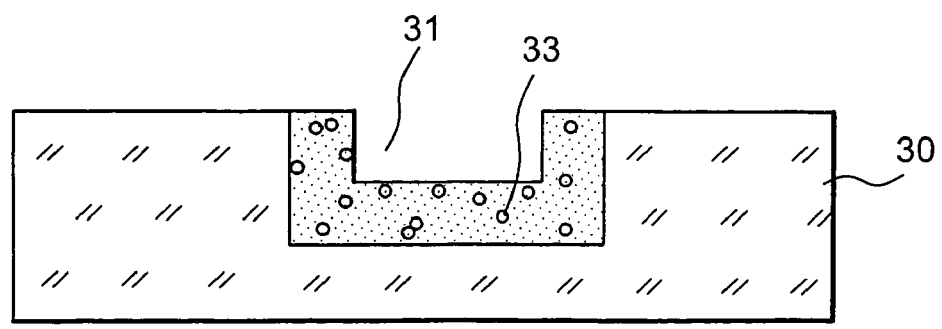

FIGS. 3A and 3B illustrate the formation of a component for biological or biochemical analysis microsystems for which the composite material is confined in a channel.

FIG. 3A shows a support 30 in polymer in which one face has an impression 31 formed by a conventional technique such as embossing, moulding or laser ablation. A layer 32 of composite material is deposited on the surface having an impression while covering the walls of said impression. The composite material is formed of a commercially available photosensitive polyimide called "Probimide 7510" in which are dispersed microbeads, for example 1 μm diameter silica microbeads. The composite material is deposited by dipping than annealed at 110° C. on a heating plate.

The deposited composite material is radiated, through a mask, by ultra violet rays then developed in order to obtain the desired component, represented in FIG. 3B. For said component, only the walls of the impression 31 are covered with a layer 33 of composite material. Said composite material is then annealed at 150° C. on a heating plate, then at 300° C. in a thermal treatment oven.

Figure 4A:
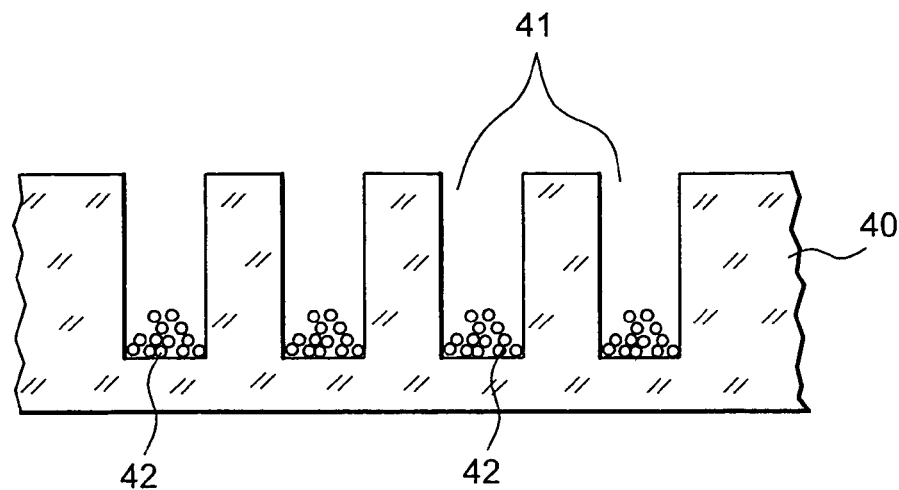
FIGS. 4A to 4C are cross-sectional views illustrating the formation of a fourth component for biological or biochemical analysis microsystems according to the invention.
Figure 4B:
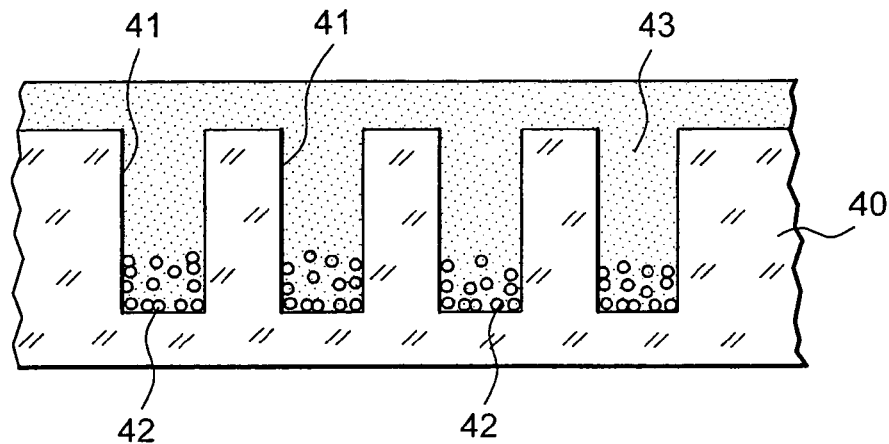
Figure 4C:
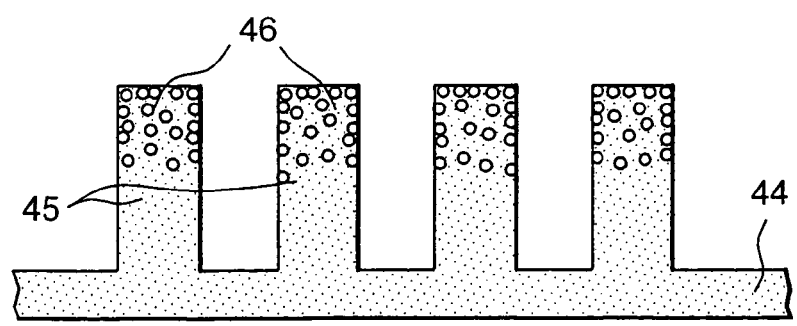

FIGS. 4A to 4C illustrate the formation of a component for biological or biochemical analysis microsystems where the composite material is obtained by deposition of inert material on a bed of beads.

FIG. 4A shows a support 40, for example a support in silicon of 100 mm diameter, in which the upper face has been machined or etched to form an impression consisting in a series of parallel trenches 41. One deposits at the base of said trenches 41 beads 42 in silica of 100 μm diameter.

As shown in FIG. 4B, an inert material 43, for example a poly (dimethylsiloxane), is poured on the support 40. Said inert material fills the trenches 41 and mixes with the beads 42 at the base of the trenches.

The whole is then placed in an oven at 60° C. for 4 hours. After evacuation of the solvents contained in the polymer, one carries out the unmoulding. One obtains the component represented in FIG. 4C formed of a base 44 and walls 45, the summit 46 of said walls being in composite material. The component is ready to undergo chemical protocols allowing it to be functionalised.

One may use previously functionalised beads such as those that are commercially available. Said beads have on their surface chemical functions (acid, amine, aldehydes) or biological groups (avidin, biotin). Said functionalised beads are then mixed with the inert material in order to form a composite material comprising an inert phase and a functionalised phase.

Depending on the nature of the functionalisable material, different techniques may be used to functionalise it. In the case of materials such as silicon, silicon oxide, silicon nitride or synthetic silica, a silanisation treatment makes it possible to attach to the surface of said materials chemical functions that will subsequently assure the attachment of biological elements or chemical functions.

Different types of silane may be used. Each has its own protocol for attachment to the surface of the material to be functionalised. The choice of silane to use depends on the chemical function that one wishes to use either directly or for the subsequent carrying out of a chemical reaction or the attachment of a biological element. Among the most commonly used silanes, one may cite aminopropyl triethoxysilane, aminopropyl dimethylethoxysilane, epoxy silane, 2-(hydroxyethyl)-3-aminopropyl triethoxysilane.

By way of example, the silanisation protocol used for aminopropyl triethoxysilane is as follows:
  treating the surface concerned by an oxygen plasma (Nextral 310) at 150 watts for 30 seconds to create silanol functions on the surface;
  incubating in a 10% silane solution in 95% ethanol for 12 hours;
  rinsing in distilled water;
  rinsing in 95% ethanol;
  annealing at 110° C. for 3 hours in an oven.

One may directly attach synthesized oligonucleotides with an aldehyde function or by the intermediary of a glutaraldehyde if the oligonucleotides have been synthesized with an $NH_2$ function.

This silanisation technique makes it possible to attach oligonucleotides, proteins or any biological or chemical element compatible with the functions present on the silane attached to the functionalised material (amine, aldehyde acid, activated ester functions, etc.).

If the material to be functionalised is a layer of gold, one uses the attachment of thiols or disulphide compounds on the surface of said metallic layer. As for silanes, different thiols make it possible to obtain on the surface of the layer to be functionalised the chemical functions necessary for the desired chemical reactions. The techniques for attaching thiols on a metallic surface are known, for example through the following document "*Formation of Monolayer Films by Spontaneous Assembly of Organic Thiols from Solution onto Gold*" by C. D. BAIN et al., J. Am. Chem. Soc., 1989, Vol. III, N° 1, pages 321 to 335.

Again by way of example, one may cite the grafting of mercapto-propionic acid or cystamin by incubating a 1 mM solution for 3 hours in absolute ethanol at ambient temperature.

For an electrical functionalisation, one may obtain electrical charges on the surface of synthetic silica, silicon, silicon nitride or silicon oxide by grafting an aminopropyl triethoxysilane on the layer to be functionalised according to the protocol described here-above. A treatment in acid medium (for example 0.2 M HCl) makes it possible to protect the amine group of the silane and obtain electrical charges on the surface of the functionalised material.

The invention claimed is:

1. Component for biological or biochemical analysis microsystems formed from a support and having at least one surface zone chemically functionalised and/or electrically functionalised, the chemical functionalisation allowing in said zone the formation of a chemistry for anchoring biological or biochemical elements, the electrical functionalisation allowing in said zone the formation of electrical charges, in which said support comprises at least one part formed of a composite material, said composite being a mixture of at least one inert material and at least one chemically and/or electrically functionalisable material to provide said functionalised surface zone, wherein the inert material is a polymer which is a polymide, a poly (dimethylsiloxane) or a photosensitive epoxy resin.

2. Component according to claim 1, in which said part forms the support in its entirety.

3. Component according to claim 1, in which the support comprises a substrate supporting said part.

4. Component according to claim 3, in which the substrate is in a material chosen from among glass, silica, silicon, a polymer and a metal.

5. Component according to claim 1, in which the functionalisable material is chosen from among silica, synthesised silica, silicon nitride, a metal and a functionalisable polymer.

6. Component according to claim 1, in which the composite material is a mixture comprising a phase of inert material and a phase of functionalisable material.

7. Component for biological or biochemical analysis microsystems formed from a support and having at least one surface zone chemically functionalised and/or electrically functionalised, the chemical functionalisation allowing in said zone the formation of a chemistry for anchoring biological or biochemical elements, the electrical functionalisation allowing in said zone the formation of electrical charges, in which said support comprises at least one part formed of a composite material, said composite being a mixture of at least one inert material and at least one chemically and/or electrically functionalisable material to provide said functionalised surface zone, wherein the composite material is formed of beads of a functionalisable material dispersed in the inert material.

* * * * *